US009364674B2

(12) United States Patent
Cook et al.

(10) Patent No.: US 9,364,674 B2
(45) Date of Patent: Jun. 14, 2016

(54) PULSE GENERATOR FOR CRANIAL NERVE STIMULATION

(76) Inventors: Ian A. Cook, Los Angeles, CA (US); Christopher M. DeGiorgio, Valencia, CA (US); Leon Ekchian, Glendale, CA (US); Patrick Miller, Santa Monica, CA (US); Colin Kealey, Los Angeles, CA (US)

( * ) Notice: Subject to any disclaimer, the term of this patent is extended or adjusted under 35 U.S.C. 154(b) by 0 days.

(21) Appl. No.: 13/990,348

(22) PCT Filed: Nov. 30, 2011

(86) PCT No.: PCT/US2011/062714
§ 371 (c)(1),
(2), (4) Date: Dec. 3, 2013

(87) PCT Pub. No.: WO2012/075192
PCT Pub. Date: Jun. 7, 2012

(65) Prior Publication Data
US 2014/0081353 A1    Mar. 20, 2014

Related U.S. Application Data

(60) Provisional application No. 61/418,382, filed on Nov. 30, 2010.

(51) Int. Cl.
*A61N 1/37*    (2006.01)
*A61N 1/36*    (2006.01)
(Continued)

(52) U.S. Cl.
CPC .......... *A61N 1/36128* (2013.01); *A61N 1/0456* (2013.01); *A61N 1/36025* (2013.01); *A61N 1/3758* (2013.01); *A61N 1/37235* (2013.01); *A61N 1/37247* (2013.01)

(58) Field of Classification Search
CPC .......... A61N 1/36128; A61N 1/36142; A61N 1/36167; A61N 1/0456; A61N 1/36025; A61N 1/37235; A61N 1/3758; A61N 1/37247
USPC .................................................. 607/45, 59, 60
See application file for complete search history.

(56) References Cited

U.S. PATENT DOCUMENTS 3,279,468 A    10/1966    Le Vine
4,233,986 A    11/1980    Tannenbaum
(Continued)

FOREIGN PATENT DOCUMENTS

JP    2008-516696 A    5/2008
JP    2008-246040 A    10/2008
(Continued)

OTHER PUBLICATIONS

Ahmed, H. E. et al. "Use of Percutaneous Electrical Nerve Stimulation (PENS) in the Short-term Management of Headache". Headache, 40:311-315 (2000).
(Continued)

*Primary Examiner* — Christopher D Koharski
*Assistant Examiner* — Michael Carey

(57) ABSTRACT

A system for trigeminal nerve stimulation includes a storage medium, a pulse generator in communication with the storage medium, a power source coupled to the pulse generator, and at least one electrode communicatively coupled to the pulse generator. The pulse generator includes a microcontroller which executes instructions from the storage medium and the microcontroller is configured to perform at least one of the following operations: produce electrical pulses having defined characteristics, record a log of use and anomalous events, restrict use to a specified individual, interface with electrodes, provide a signal to the specified individual indicating operational conditions and trouble conditions, and provide a signal to the specified individual indicating an end of a treatment period.

17 Claims, 16 Drawing Sheets

(51) Int. Cl.
*A61N 1/04* (2006.01)
*A61N 1/372* (2006.01)
*A61N 1/375* (2006.01)

(56) References Cited

U.S. PATENT DOCUMENTS

| | | | |
|---|---|---|---|
| 4,635,641 | A | 1/1987 | Hoffman |
| 5,514,175 | A | 5/1996 | Kim et al. |
| 5,540,734 | A | 7/1996 | Zabara |
| 6,405,079 | B1 | 6/2002 | Ansarinia |
| 6,567,702 | B1 | 5/2003 | Nekhendzy et al. |
| 6,735,475 | B1 | 5/2004 | Whitehurst et al. |
| 6,950,707 | B2 | 9/2005 | Whitehurst |
| 6,954,668 | B1 | 10/2005 | Cuozzo |
| 7,171,276 | B2 | 1/2007 | Giuntoli et al. |
| 7,502,652 | B2 | 3/2009 | Gaunt et al. |
| 7,734,340 | B2 | 6/2010 | De Ridder |
| 7,801,601 | B2 | 9/2010 | Maschino et al. |
| 8,380,315 | B2 | 2/2013 | DeGiorgio et al. |
| 8,428,734 | B2 | 4/2013 | Rigaux et al. |
| 8,494,641 | B2 | 7/2013 | Boling et al. |
| 8,512,715 | B2 | 8/2013 | Papay |
| 8,554,324 | B2 | 10/2013 | Brocke |
| 8,565,896 | B2 | 10/2013 | Ben-David et al. |
| 8,591,419 | B2 | 11/2013 | Tyler |
| 8,666,498 | B2 | 3/2014 | Newman |
| 8,688,220 | B2 | 4/2014 | DeGiorgio et al. |
| 8,700,164 | B2 | 4/2014 | DeGiorgio et al. |
| 2002/0077670 | A1 | 6/2002 | Archer et al. |
| 2004/0138097 | A1 | 7/2004 | Guyuron |
| 2004/0176820 | A1 | 9/2004 | Paul |
| 2004/0243207 | A1 | 12/2004 | Olson et al. |
| 2005/0283198 | A1 | 12/2005 | Haubrich |
| 2006/0064140 | A1 | 3/2006 | Whitehurst et al. |
| 2006/0167500 | A1 | 7/2006 | Towe et al. |
| 2006/0173510 | A1 | 8/2006 | Besio et al. |
| 2006/0200208 | A1* | 9/2006 | Terry et al. .............. 607/58 |
| 2006/0206165 | A1 | 9/2006 | Jaax et al. |
| 2006/0293723 | A1 | 12/2006 | Whitehurst et al. |
| 2007/0049988 | A1 | 3/2007 | Carbunaru et al. |
| 2007/0060975 | A1 | 3/2007 | Mannheimer et al. |
| 2007/0150025 | A1 | 6/2007 | Dilorenzo et al. |
| 2007/0150027 | A1 | 6/2007 | Rogers |
| 2007/0173908 | A1 | 7/2007 | Begnaud |
| 2007/0179557 | A1 | 8/2007 | Maschino et al. |
| 2007/0233194 | A1 | 10/2007 | Craig |
| 2007/0276451 | A1 | 11/2007 | Rigaux |
| 2008/0046013 | A1 | 2/2008 | Lozano |
| 2008/0103547 | A1 | 5/2008 | Okun et al. |
| 2008/0128215 | A1 | 6/2008 | Nowitz |
| 2008/0132980 | A1 | 6/2008 | Gerber et al. |
| 2008/0140151 | A1 | 6/2008 | Brodkey |
| 2008/0147141 | A1 | 6/2008 | Testerman et al. |
| 2008/0161713 | A1 | 7/2008 | Leyde et al. |
| 2008/0171929 | A1 | 7/2008 | Katims |
| 2008/0172101 | A1 | 7/2008 | Bolea et al. |
| 2008/0269716 | A1 | 10/2008 | Bonde et al. |
| 2008/0275327 | A1 | 11/2008 | Faarbaek et al. |
| 2009/0048642 | A1 | 2/2009 | Goroszeniuk |
| 2009/0210028 | A1 | 8/2009 | Rigaux et al. |
| 2009/0287035 | A1 | 11/2009 | Dietrich et al. |
| 2010/0030227 | A1 | 2/2010 | Kast et al. |
| 2010/0198044 | A1 | 8/2010 | Gehman et al. |
| 2010/0198282 | A1 | 8/2010 | Rogers |
| 2010/0222847 | A1 | 9/2010 | Goetz |
| 2010/0228105 | A1 | 9/2010 | Policker et al. |
| 2010/0228113 | A1 | 9/2010 | Solosko et al. |
| 2010/0262205 | A1 | 10/2010 | De Ridder |
| 2011/0093033 | A1 | 4/2011 | Nekhendzy |
| 2011/0106220 | A1 | 5/2011 | DeGiorgio et al. |
| 2011/0112603 | A1 | 5/2011 | DeGiorgio et al. |
| 2011/0184489 | A1 | 7/2011 | Nicolelis et al. |
| 2011/0218589 | A1 | 9/2011 | DeGiorgio et al. |
| 2011/0218590 | A1 | 9/2011 | DeGiorgio et al. |
| 2011/0282129 | A1 | 11/2011 | Rigaux |
| 2011/0282412 | A1 | 11/2011 | Glukhovsky et al. |
| 2011/0288610 | A1* | 11/2011 | Brocke ............... A61M 21/02 607/45 |
| 2012/0203301 | A1 | 8/2012 | Cameron et al. |
| 2012/0330380 | A1* | 12/2012 | Corndorf ................... 607/60 |
| 2013/0158626 | A1 | 6/2013 | DeGiorgio et al. |
| 2014/0046407 | A1 | 2/2014 | Ben-Ezra et al. |
| 2014/0081353 | A1 | 3/2014 | Cook et al. |
| 2014/0081369 | A1 | 3/2014 | Sosa et al. |

FOREIGN PATENT DOCUMENTS

| | | |
|---|---|---|
| JP | 2009-531154 A | 9/2009 |
| JP | 4961558 B2 | 6/2012 |
| JP | 2003-339884 A | 12/2013 |
| RU | 2086227 C1 | 8/1997 |
| RU | 2185092 C1 | 7/2002 |
| SU | 1718976 A1 | 3/1992 |
| WO | WO 2006/044793 A2 | 4/2006 |
| WO | WO 2007/136726 | 11/2007 |
| WO | WO 2008/128215 A1 | 10/2008 |
| WO | WO 2009/158389 | 12/2009 |
| WO | WO 2011/044173 | 4/2011 |
| WO | WO 2011/044176 | 4/2011 |
| WO | WO 2011/044178 | 4/2011 |
| WO | WO 2011/044179 | 4/2011 |
| WO | WO 2012/075192 A2 | 6/2012 |
| WO | WO 2012/082960 | 6/2012 |
| WO | WO 2012/082961 | 6/2012 |
| WO | WO 2013/104552 A1 | 7/2013 |
| WO | WO 2013/152316 A1 | 10/2013 |

OTHER PUBLICATIONS

Allais, G. et al., "Non-pharmacological approaches to chronic headaches: transcutaneous electrical nerve stimulation, lasertherapy and acupuncture in transformed migraine treatment". Neuro Sci, 24:S138-S142 (2003).

DeGiorgio, C. et al., "Trigeminal nerve stimulation for epilepsy." Neurology, 61:421-422 (2003).

DeGiorgio, C. et al., "Pilot Study of Trigeminal Nerve Stimulation (TNS) for Epilepsy: A Proof-of-Concept Trial". Epilepsia, 47(7): 1213-1215 (2006).

Moseley, B.D. and DeGiorgio, C., "Refractory status epilepticus treated with trigeminal nerve stimulation." Epilepsy Research, 108: 600-603 (2014).

* cited by examiner

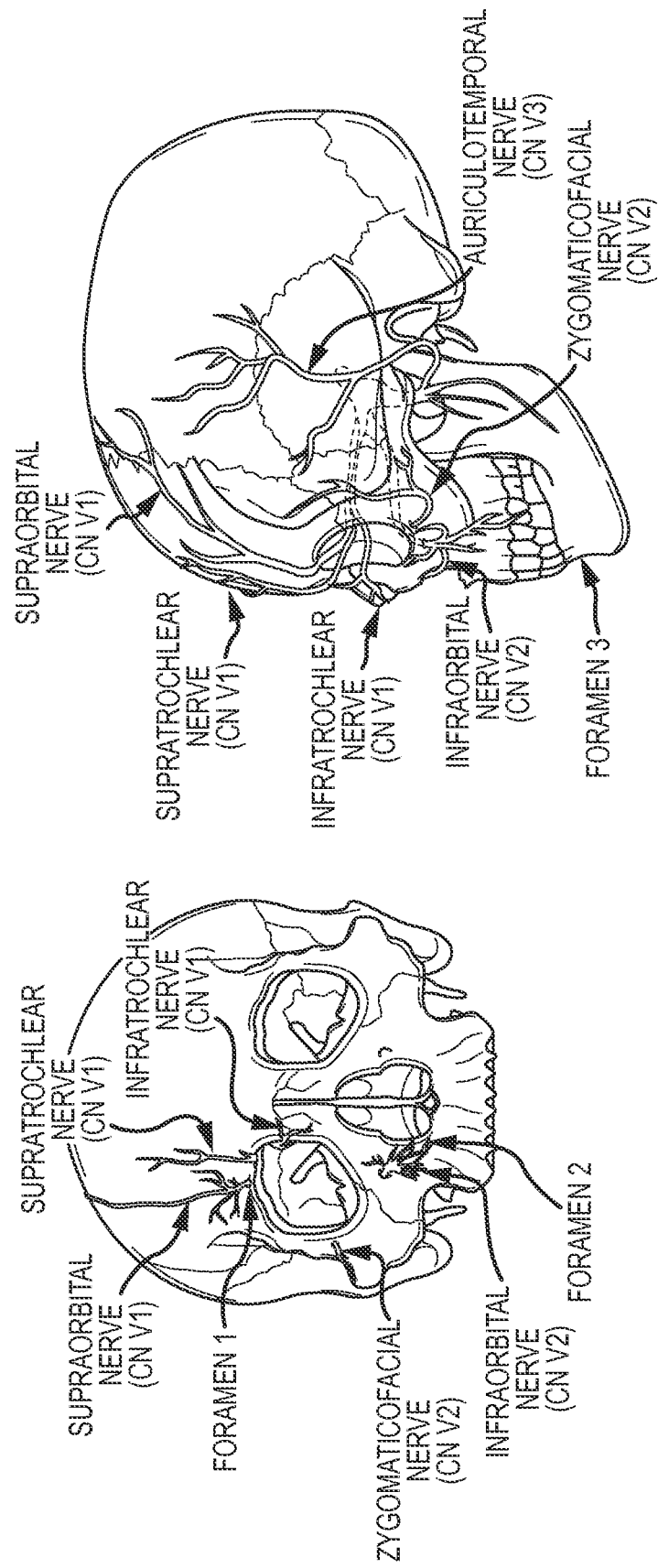

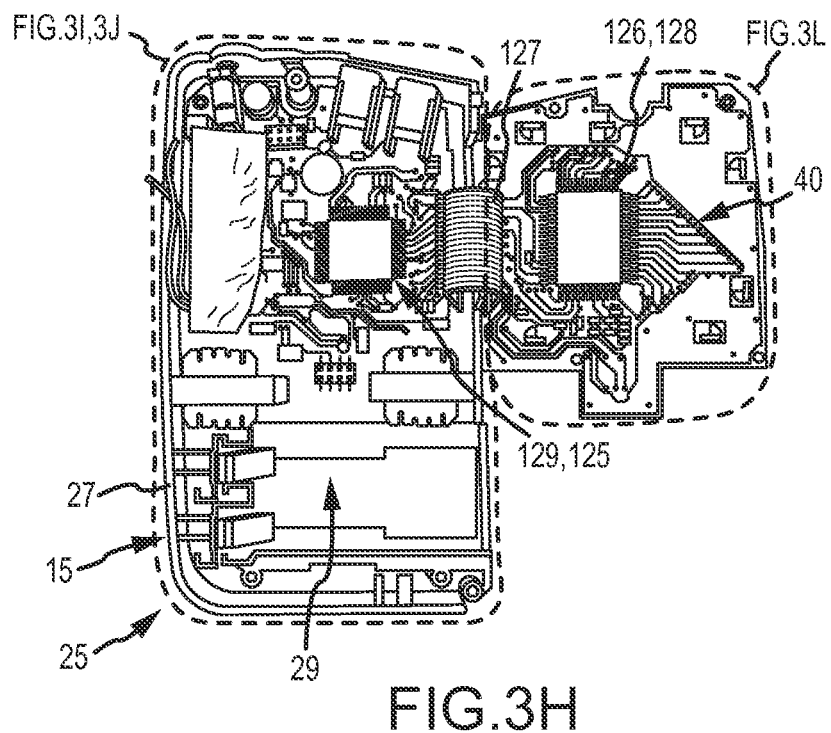

PULSE GENERATOR FOR CRANIAL NERVE STIMULATION

CROSS REFERENCE TO RELATED APPLICATIONS

This Application is a U.S. National Stage filing under 35 U.S.C. §371 of PCT Patent Application No. PCT/US2011/062714, filed Nov. 30, 2011, which claims priority to U.S. Provisional Patent Application No. 61/418,382, filed on Nov. 30, 2010. The contents of the aforementioned applications are incorporated by reference herein. Priority is expressly claimed in accordance with 35 U.S.C. §§119, 120, 365 and 371 and any other applicable statutes.

FIELD

The present disclosure generally relates to external neurostimulator devices and methods of using the same and more particularly relates to external neurostimulator devices configured to stimulate the superficial (cutaneous) sensory branches of cranial nerves.

BACKGROUND

Currently available surgical treatment methods for certain medical disorders, such as epilepsy or other seizure related disorders, may include stimulation of the nervous system by vagus nerve stimulation (VNS), which has been approved by the U.S. Food and Drug Administration (FDA). In this method, stimulating electrodes are surgically implanted in contact with the vagus nerve as it passes through the neck. In addition to complications related to anesthesia, potential for infection, cost, and other adverse events with VNS, many of the subjects who undergo VNS treatments do not achieve relief, and there is no reliable predictor of good outcomes from the implanted VNS device.

Other approaches to neuromodulation are the focus of on-going research. For example, implantable approaches are also being studied, including deep brain stimulation (DBS) of specific brain regions, and intracranial stimulation of the same via a device which monitors brain activity and delivers stimuli as needed. However, the risks of DBS include infection, hemorrhage, and injury to deep brain structures.

In some clinical situations, electroconvulsive therapy (ECT) and repetitive transcranial magnetic stimulation (rTMS) have been used for neurological and psychiatric conditions. Traditionally, brain stimulation has been a primary treatment alternative to medications and psychotherapy, and ECT has been the dominant brain stimulation approach since the first part of the 20th century. However, ECT carries risks of memory and other cognitive side effects, considerable cost, and risks of anesthesia.

Many of the above-described methods are invasive and may have considerable costs and side effects. Further, a substantial percentage of patients do not recover from or get adequate lasting relief for the condition or disorder despite multiple trials of pharmaceutical or surgical treatment.

The information included in this Background section of the specification, including any references cited herein and any description or discussion thereof, is included for technical reference purposes only and is not to be regarded as subject matter by which the scope of the invention is to be bound.

SUMMARY

One aspect of the subject matter of the present disclosure addresses the aforementioned needs by providing a system and device configured to stimulate the trigeminal nerve that is minimally invasive and has reduced side effects in comparison with other neuromodulation approaches.

Disclosed herein is a system for trigeminal nerve stimulation. In one embodiment, the system includes a storage medium, a pulse generator communicatively coupled to the storage medium, a power source coupled to the pulse generator, and at least one electrode communicatively coupled to the pulse generator. The pulse generator includes a microcontroller which executes instructions from the storage medium and the microcontroller is configured to perform at least one of the following operations: produce electrical pulses having defined characteristics, record a log of use and anomalous events, restrict use to a specified individual, interface with electrodes, provide a signal to the specified individual indicating operational conditions and trouble conditions, and provide a signal to the specified individual indicating an end of a treatment period. In some embodiments, the system may further include a power supply or charging station. The power source may be a battery, such as a rechargeable battery.

Disclosed herein is a pulse generator for trigeminal nerve stimulation. In one embodiment, the generator includes a body having a front and back portion and includes at least one electrode channel. The pulse generator also includes a power source. The pulse generator also includes at least one microcontroller executing instructions from a storage medium and the microcontroller is configured to perform at least one of the following operations: produce electrical pulses having defined characteristics, record a log of use and anomalous events, restrict use to a specified individual, interface with electrodes, provide a signal to the specified individual indicating operational conditions and trouble conditions, and provide a signal to the specified individual indicating an end of a treatment period. The pulse generator further includes a display configured to provide a graphical user interface and at least one user control feature configured to allow a user to control at least one operation of the pulse generator. The pulse generator may further include a power inlet port defined in the body. In one embodiment, the body has dimensions of approximately 115 mm (4.5 in) H×69 mm (2.7 in) W×27 mm (1.1 in) D and a weight of 145 g (5.1 oz) without a battery. In some embodiments, the power source may be a battery and the body may include at least one battery cavity defined in the back portion of the body that is configured to accept a battery. In one embodiment, the body is plastic, metal alloy or composite material. In one aspect, the microcontroller limits output current and the current is limited to approximately less than 35 mA. In various embodiments, the current output has an upper limit of approximately 10 mA, 7 mA or 5 mA. In some embodiments, the current output has a lower limit of approximately 2.5 mA. In some embodiments, the current output is fixed at approximately 5 mA. In one embodiment, the microcontroller is configured to deliver (or delivers) a true square-wave charge-balanced output signal or a non-rectangular output signal. In one aspect, the microcontroller produces electrical pulses having the following characteristics: frequency 1-300 Hz, pulse duration 50-500 usec, duty cycle 1-100%. In one aspect, the electrode channel comprises at least one groove configured to accept at least one projection located at an end of a lead wire of the electrode assembly to form a lock and key configuration. In one aspect, the electrode channel is keyed for a specific electrode assembly.

Disclosed herein is a method for operating a pulse generator having a processing device for stimulating at least one cutaneous trigeminal nerve branch using the pulse generator. In one embodiment, the method includes receiving instructions from a storage medium and performing at least one of the following operations: producing electrical pulses having defined characteristics, recording a log of use and anomalous events, restricting use to a specified individual, interfacing with specialized electrodes, providing a signal to the specified individual indicating operational conditions and trouble conditions, and providing a signal to the specified individual indicating an end of a treatment period. In one aspect, the operation of restricting use to a specified individual comprises requiring a patient user to provide a personal identification number (PIN) or a biometric ID to operate the pulse generator. In one aspect, the PIN is a five digit number and the biometric ID is a fingerprint. In one aspect, the operation of producing electrical pulses having defined characteristics is performed by a microcontroller and the characteristics are frequency 1-300 Hz, pulse duration 50-500 usec, duty cycle 1-100%. In one aspect, the operation of interfacing with electrodes is performed by at least one electrode channel defined in the pulse generator that is keyed to the electrode.

Disclosed herein is a computer-readable medium having computer-executable instructions for performing a process for stimulating a branch of a trigeminal nerve. In one embodiment, the instructions include causing a processor device to produce electrical pulses having defined characteristics, record a log of use and anomalous events, restrict use to a specified individual, interface with specified electrodes, provide a signal to the specified individual indicating operational conditions and trouble conditions, and provide a signal to the specified individual indicating an end of a treatment period.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

The present disclosure, both as to its organization and manner of operation, may be understood by reference to the following description, taken in connection with the accompanying drawings, in which:

FIGS. 1A and 1B illustrate the location of several branches (nerves) of the trigeminal nerve and the location of the major foramina for the superficial branches of the trigeminal nerve;

FIG. 3E-2 is a top plan view of the pulse generator of FIG. 3A;

FIG. 3F-1 and FIG. 3F-2 depict top plan views of the inside front and back portions of the housing of the pulse generator of FIG. 3A;

FIG. 3H is the pulse generator of FIG. 3G wherein the electrical components beneath the display are shown;

DETAILED DESCRIPTION

Figure 2A:
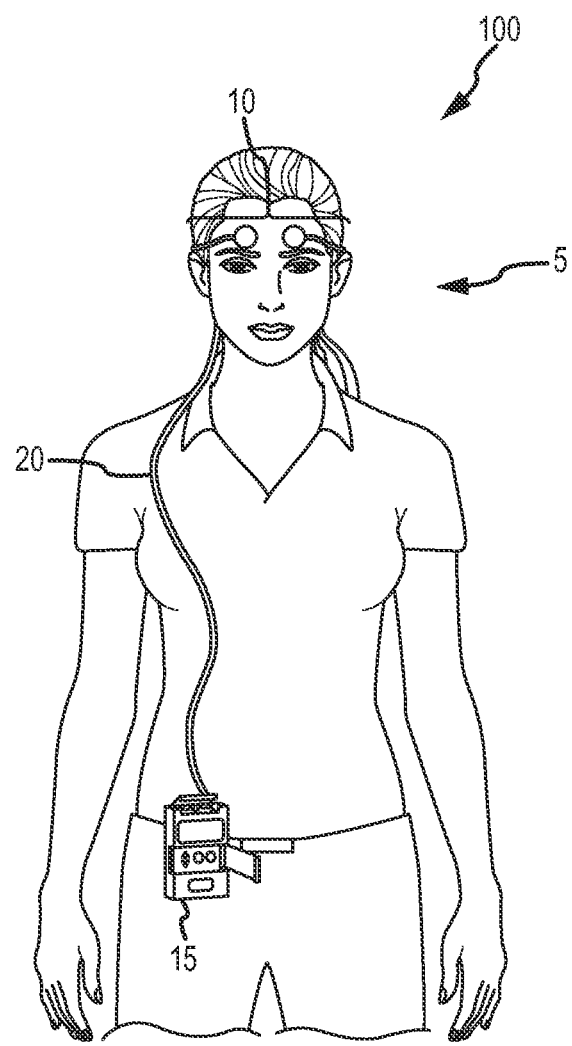
FIG. 2A depicts an example of a subject wearing one embodiment of an electrode assembly and pulse generator according to aspects of the present disclosure.

The present disclosure relates to a device configured for stimulation of the sensory branches of the trigeminal nerve in the face and forehead (trigeminal nerve stimulation or TNS). More specifically, an external pulse generator or neurostimulator configured for stimulation of the sensory components of the ophthalmic nerve and its branches, the infraorbital nerve and its branches, and the mentalis nerves or its branches, and including the supraorbital, supratrochlear, infraorbital, auriculotemporal, zygomaticotemporal, zygomaticoorbital, zygomaticofacial, nasal and infratrochlear nerves is disclosed herein. The pulse generator may be used to treat various disorders, such as neurological disorders as disclosed in, for example, co-pending U.S. patent application Ser. No. 12/898,675 (now U.S. Pat. No. 8,688,220) entitled Systems, Devices and Methods for the Treatment of Neurological Disorders and Conditions, and psychiatric disorders as disclosed in, for example, co-pending U.S. patent application Ser. No. 12/898,686 (now U.S. Pat. No. 8,380,315) entitled Devices, Systems and Methods for Treatment of Neuropsychiatric Disorders, both of which are hereby incorporated by reference in their entireties.

In previous studies, a commercially available TENS unit, the EMS 7500, has been used. The TENS unit is designed to deliver currents up to 100 mA, well above the levels needed for external TNS. In clinical use for TNS for epilepsy, for example, the high currents would present a potential safety hazard to patients, both for dermal injury and the passage of current through the skull and injuring the brain parenchyma. The pulse generator or neurostimulator as disclosed herein is configured to limit the current delivered and includes a programmable microcontroller to implement the features disclosed herein, thereby reducing the potential for patient injury and optimizing ease of use (user friendliness).

The pulse generator as disclosed herein includes a programmable microcontroller which, in various embodiments, may implement some or all of the following features: produces electrical pulses of specific, programmable characteristics; records a log of use and anomalous events; restricts use to a specified individual; interfaces with various electrode designs, including both subcutaneous implantable electrode designs, such as those described in co-pending U.S. patent application Ser. No. 12/898,685 (now U.S. Patent Application Publication No. US 2011-0112603 and currently pending) and Ser. No. 12/898,696 (now U.S. Patent Application Publication No. US 2011-0106220 and currently pending), both of which are hereby incorporated by reference, and cutaneous electrode designs, such as those described in the above-mentioned '675 and '686 applications; signals the patient-user (or a physician or other care provider) about operational conditions and trouble conditions; signals the need for a physician reprogramming visit with weekly warning signals and suspending operations until reprogrammed at the specified date; and is rechargeable and is sealed to protect against, for example, liquid penetration into the internal structure of the pulse generator. In some embodiments, the pulse generator may signal a physician or other care provider over the internet or cell phone and the communication may be in real time. In some embodiments, the pulse generator can inform a physician or other care provider that the patient may be having a seizure (based on processing implanted or external EEG data, or other physiologic data such as autonomic nervous system indices (e.g. heart rate variability)) or that the patient has fallen (based on processing data from an accelerometer built into the pulse generator or implanted in the patient).

The unique anatomy of the trigeminal nerve, and its direct and indirect projections to key areas of the brainstem, thalamus and cortex involved with sensory processing, attention, and autonomic function, may allow the use of stimulation by a pulse generator as disclosed herein for a variety of neurological, psychiatric and other conditions in which stimulation may be desirable.

For a discussion related to the trigeminal nerve, reference is now made to FIGS. 1A-1B, which illustrate the location of several branches of the trigeminal nerve and the location of the major foramina for the superficial branches of the trigeminal nerve. The trigeminal nerve is the largest cranial nerve and has extensive connections with the brainstem and other brain structures. As it is the fifth of the twelve cranial nerves, it is also known interchangeably as CN V. The trigeminal nerve has three major sensory branches over the face, all of which are bilateral, and highly accessible. The supraorbital nerve, or ophthalmic nerve, is frequently referred to as the $V_1$ division. The infraorbital branch, or the maxillary nerve, is commonly referred to as the $V_2$ division. The superficial branch, or the mandibular nerve (also known as the mentalis branch), is referred to as the $V_3$ division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the jaw, tongue, and lower lip.

As can be understood from FIGS. 1A and 1B, these branches exit the skull through three foramina. The supraorbital nerve or ophthalmic nerve exits at foramen 1 (the supraorbital foramen or notch), approximately 2.1-2.6 cm from the nasal midline (in adults), and is located immediately above the orbital ridge that is near the eyebrow. The nasal nerve is a division of the ophthalmic nerve. The infraorbital branch or maxillary nerve exits at foramen 2 (the infraorbital foramen), approximately 2.4-3.0 cm from the nasal midline (in adults) and the mentalis nerve exits at foramen 3 (the mentalis foramen) approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of Cranial Nerve V, and the spinal nucleus and tract of V. Pain fibers descend in the spinal nucleus and tract of V, and then ascend to the ventral posterior medial nucleus (VPM) of the thalamus and then project to the cerebral cortex. Light touch sensory fibers are large myelinated fibers, which ascend to the ventral posterior lateral (VPL) nucleus of the thalamus. Afferent sensory fibers project from the trigeminal nuclei to the thalamus and the cerebral cortex.

The trigeminal nucleus has projections to the nucleus tractus solitarius (NTS), the locus ceruleus, the cerebral cortex, and the vagus nerve. The NTS receives afferents from the vagus nerve and trigeminal nerve. NTS integrates input from multiple sources, and projects to structures in the brainstem and forebrain, including the locus ceruleus.

The locus ceruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus ceruleus is a core part of the brainstem noradrenergic pathway, and produces the neurotransmitter norepinephrine. Norepinephrine plays a key role in attention, alertness, blood pressure and heart rate regulation, anxiety and mood.

While not wishing to be bound by any particular theory, in certain embodiments, the connections between the trigeminal nerve, locus coeruleus, nucleus and tractus solitarius, thalamus, and cerebral cortex, may be relevant to a potential role of the trigeminal nerve in numerous disorders and conditions. Thus, cutaneous stimulation of the trigeminal nerve via a pulse generator as disclosed herein or a system that includes the pulse generator may be effective in the treatment of multiple disorders and conditions where treatment via trigeminal nerve stimulation is indicated.

Accordingly, stimulation of the superficial or cutaneous branches of the trigeminal nerve provides an avenue for non-invasive neuromodulation. Further, stimulation parameters can be tailored for the individual condition, such that the brainstem, thalamic, or cortical structures involved in the individual condition can be activated or inhibited depending on the pathophysiology of the condition being treated.

Figure 2B:
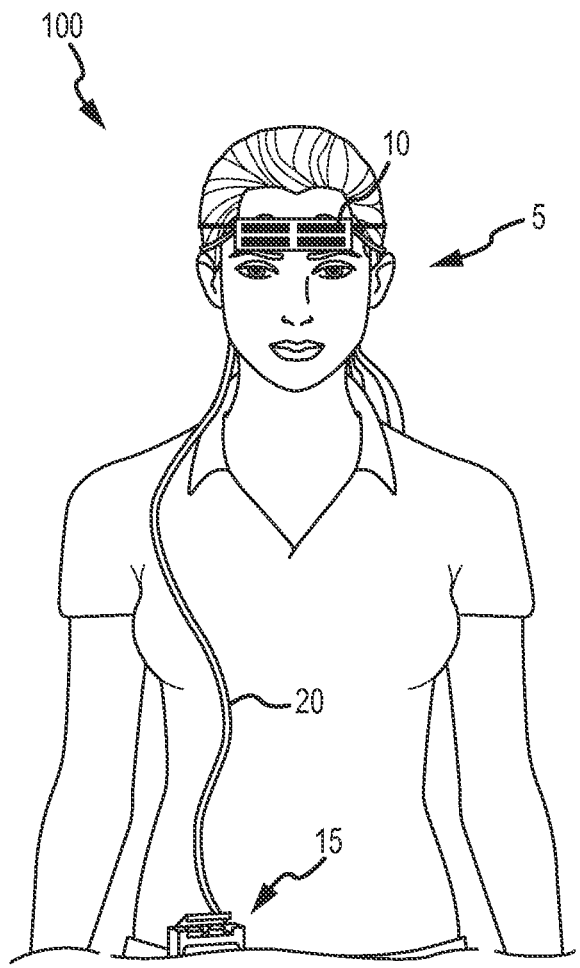
FIG. 2B depicts an example of a subject wearing another embodiment of an electrode assembly and pulse generator according to aspects of the present disclosure.

In one embodiment, as can be understood from FIGS. 2A-2B, a system 100 for stimulation of the trigeminal nerve or a branch thereof includes an electrode assembly 10, a neurostimulator or pulse generator 15 and electrical cable or wire 20. The electrode assembly 10 may be configured for the bilateral simultaneous and asynchronous stimulation of the ophthalmic nerves. In other embodiments, the electrode assembly may be configured for unilateral or bilateral stimulation of one or more branches of the trigeminal nerve as disclosed elsewhere herein. The electrode assembly 10 may include a pair of electrodes for placement on a region of the patient's face. It can be appreciated that a single electrode or multiple electrodes may be used. An electrode assembly that may be used with the present disclosure is also described in the above-mentioned '675 and '686 applications, both of which are hereby incorporated by reference. In one embodiment, the electrical cable or wire 20 is configured to provide a physical and electrical link between the generator 15 and the electrode assembly 10 via lead wires. In other embodiments, the generator 15 and the electrode assembly 10 communicate wirelessly (i.e. the wire 20 and lead wires are not used). In one embodiment, the generator 15 is portable and attached to the belt of the patient 5. In other embodiments, the generator 15 is non-portable. In some embodiments, the system 100 may include a charging station.

In one embodiment, the electrode assembly 10 is configured for bilateral stimulation of both the right and left supraorbital branches of the Trigeminal Nerve (V1) located above the eyebrows over the forehead. The electrode assembly may include both 2-contact and 4-contact electrodes. The contact areas from which the electrical stimulation will travel from the pulse generator to the patient will be placed on the forehead over the V1 branch of the trigeminal nerve bilaterally. The regions of contact are arranged such that the electrical current travels perpendicular to the two branches of the V1 branch between two conductive areas (2 contact) or such that the current travels parallel to the two pathways of the V1 branch (4 contact).

In one embodiment, the electrode assembly 10 may be configured to deliver a symmetric biphasic pulse. In other embodiments, the pulse waveform may be asymmetric and/or multiphasic.

The electrodes may be secured to the forehead by hypoallergenic biocompatible hydrogels, such as DermaFlow™ hydrogel (Axelgaard Manufacturing Co, Ltd, Fallbrook, Calif., USA). Such gels have been specifically developed for use on the skin and forehead, to minimize skin irritation, and have undergone ISO skin sensitization and histocompatibility studies in animals.

The lead wires 40 carry the electrical impulse from the pulse generator to the conductive regions of contact thereby delivering the prescribed stimulation. In one aspect, the lead wires are 13.5" lead wires that carry the electrical impulse from the pulse generator to the conductive regions of contact. The lead wires exit a single side of the pulse generator and will be bundled together. The lead wires terminate in a specialized plug that connects to the pulse generator's socket, and is configured to prevent a patient-user from connecting the electrodes to other, potentially-hazardous sources of current.

Figure 4:
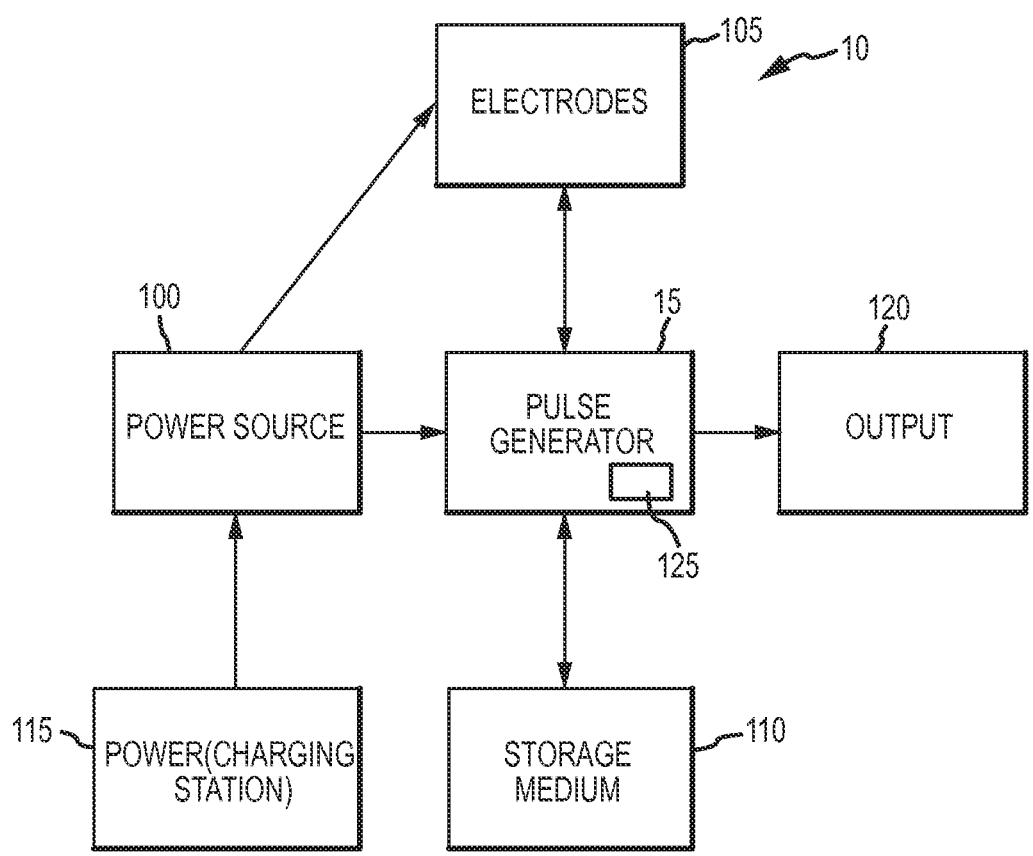
FIG. 4 is a block diagram of the system of FIG. 3.

In some embodiments, and as can be understood with reference to FIG. 4, the pulse generator 15 may also be used in conjunction with a physician docking/programming console. In other embodiments, the "programming" functions described herein may be performed directly via the user-interface described elsewhere herein. The programming docking console allows prescribing physicians to set parameters for the user/patient and to monitor the patient's use since last docking event (e.g. by uploading of logfiles). When a patient-user visits the prescribing physician, the pulse generator 15 can be programmed to administer the specific stimulation parameters prescribed by the physician by using the console, such as pulse frequency. These parameters may be set individually, or the physician may select from pre-established combinations (of, e.g., repetition frequency, pulse width, on-period/off-period). The docking/programming station may provide for selection of these parameters from menus or offer step-wise setting of parameters, within ranges and steps as allowed by the pulse generator 15. At follow-up visits, the logfiles may be examined to ascertain actual patterns of device use, as this information may be useful in treatment planning. These data may be displayed as text, or may be presented graphically, for example, as a graph showing amounts of daily use. These data may be stored for the physician to incorporate into the medical record for an individual patient.

Figure 5:
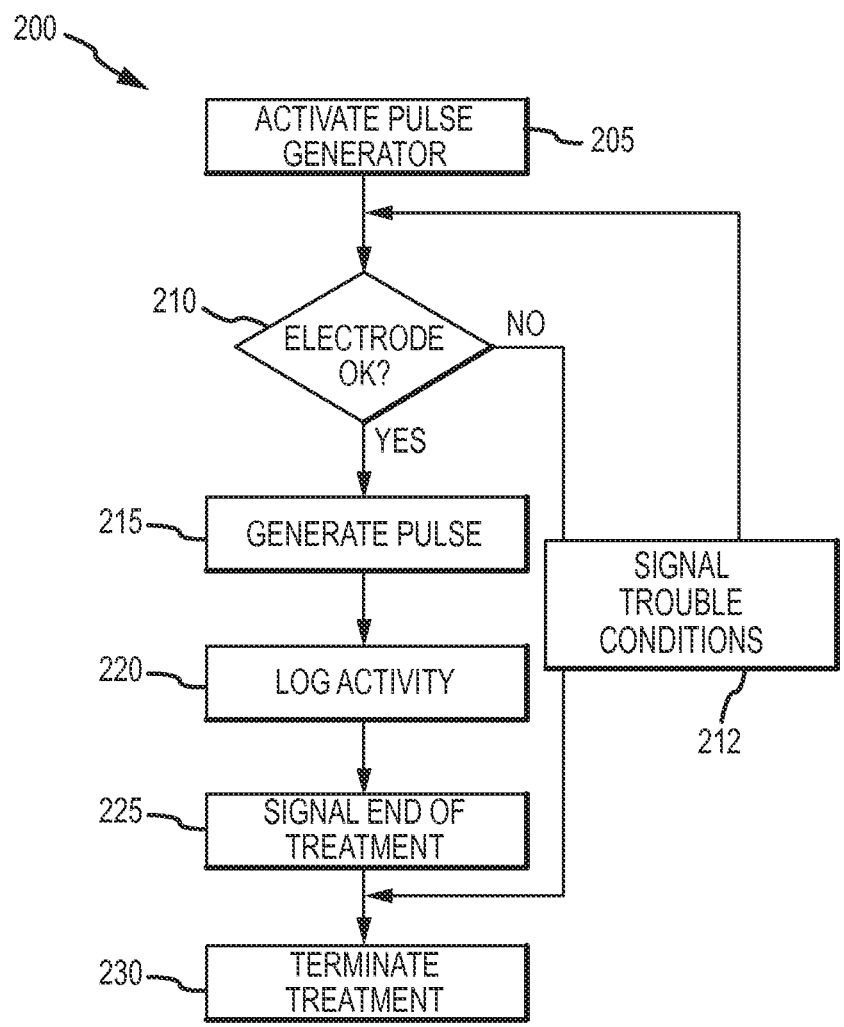
FIG. 5 is a flow chart illustrating one embodiment of a method for operation of a pulse generator.

For a more detailed discussion of the pulse generator, reference is now made to FIGS. 3A-3L, which illustrate various views of one exemplary embodiment of the pulse generator, FIG. 4, which is a block diagram depicting one embodiment of the pulse generator 15, and FIG. 5, which is a flow chart illustrating one embodiment of a method for operation of the pulse generator 15.

As can be understood from FIGS. 3A-3L, and with reference to FIGS. 4 and 5, the pulse generator 15 comprises a sealed body or case 25 which encloses or houses the internal components, such as the microcontroller and battery discussed below, and other wiring and electronic components. The pulse generator may be manufactured by ITO Co., Ltd, Japan. or other suitable manufacturer.

Figure 3A:
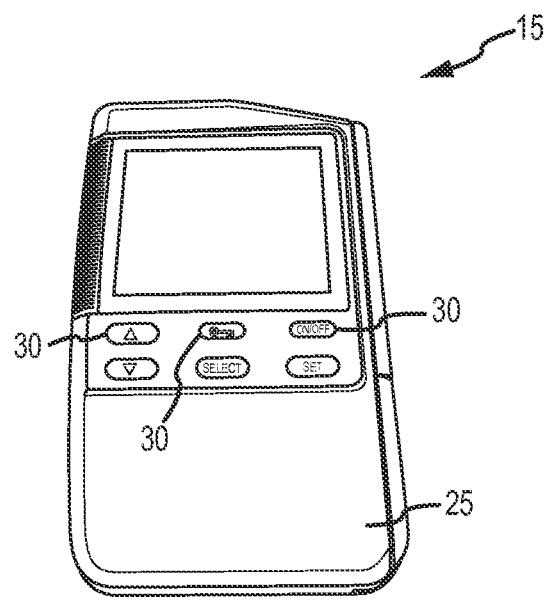
FIG. 3A is a front perspective view of another embodiment of a pulse generator according to aspects of the present disclosure.
Figure 3B:
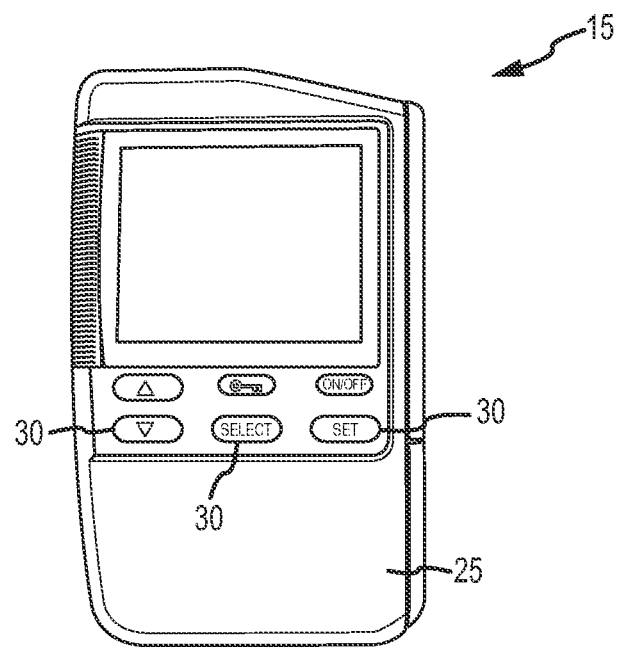
FIG. 3B is a front plan view of the pulse generator of FIG. 3A.
Figure 3C:
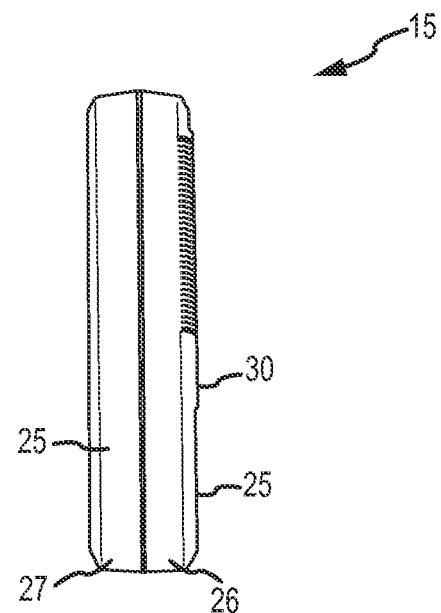
FIG. 3C is a left side view of the pulse generator of FIG. 3A.
Figure 3D:
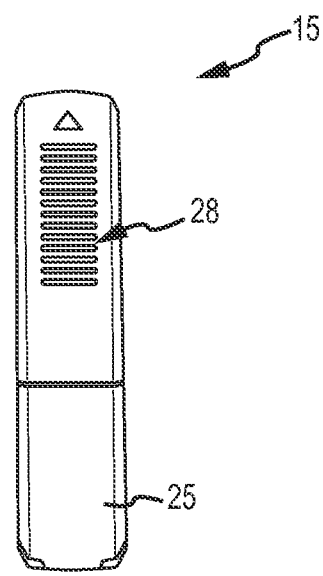
FIG. 3D is a right side view of the pulse generator of FIG. 3A.
Figures 1, 3E:
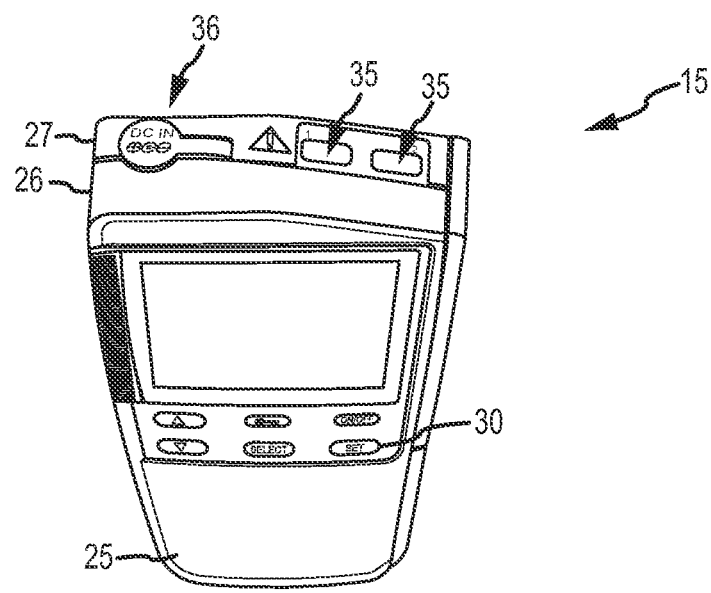
FIG. 3E-1 is a top perspective view of the pulse generator of FIG. 3A.

The sealed body 25 protects the internal components and prevents liquids, etc. from penetrating the body and damaging internal components. In one embodiment, the pulse generator 15 is housed in a rectangular hard plastic case 25 with dimensions of approximately 115 mm (4.5 in) H×69 mm (2.7 in) W×27 mm (1.1 in) D and a weight of 145 gr (5.1 oz) without a battery. In other embodiments, the body or case may be made of a metallic alloy or a composite material. As shown in FIG. 3C, and others, the body 25 includes a front portion 26 and a back portion 27. The front and back portion are sealingly engaged to prevent fluids, etc. from entering the body and interfering with the internal and electrical components housed within the body. As shown in FIGS. 3D and 3F-1, the body 25 may include raised features 28 configured to provide a gripping surface by which a user, physician, etc. can open the pulse generator to, for example, replace a battery or other electrical component. As can be seen in FIGS. 3A-3B and others, the pulse generator 15 may also include user control features 30, e.g. buttons, that allow the user to turn the power on and off or that provide a temporary lock. In some embodiments, the user control features 30 may be up and down arrow buttons that allow the patient-user to adjust the stimulus amplitude. In some embodiments, this is the only parameter which is user-adjustable (all others are controlled via the physician's programming).

As shown in FIGS. 3E-1, 3E-2, 3I-3K, and others, the pulse generator 15 may also include at least one specialized socket or channel 35 for connecting the lead wires of the electrodes. The channel 35 comprises grooves or openings 39 configured to accept an end of the lead wires of the electrode assembly. That is, the channel 39 is "keyed" for the end of the electrode or the electrode assembly. The end of the lead wire 12 includes corresponding projections 39a such that the projections 39a are received in the grooves 39 in a lock and key type configuration. This lock and key configuration prevent a patient-user from connecting the electrodes to other, potentially-hazardous sources of current and other incompatible electrode assemblies from being used with the pulse generator. In use, when a two-contact electrode is used, one channel 35 is utilized. When a four contact electrode is used, two channels 35 are utilized.

Figures 2, 3E:
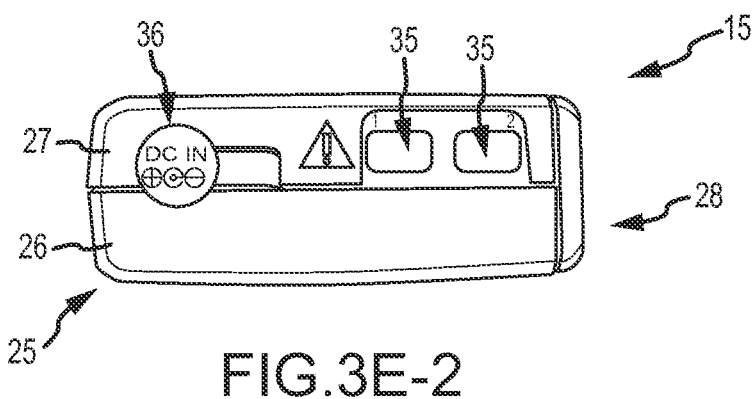
Figures 1, 3F:
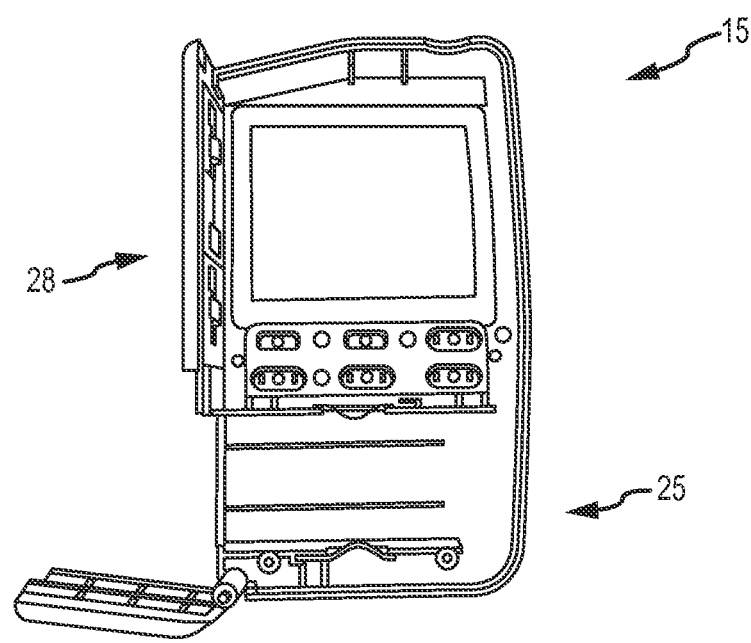
Figures 2, 3F:
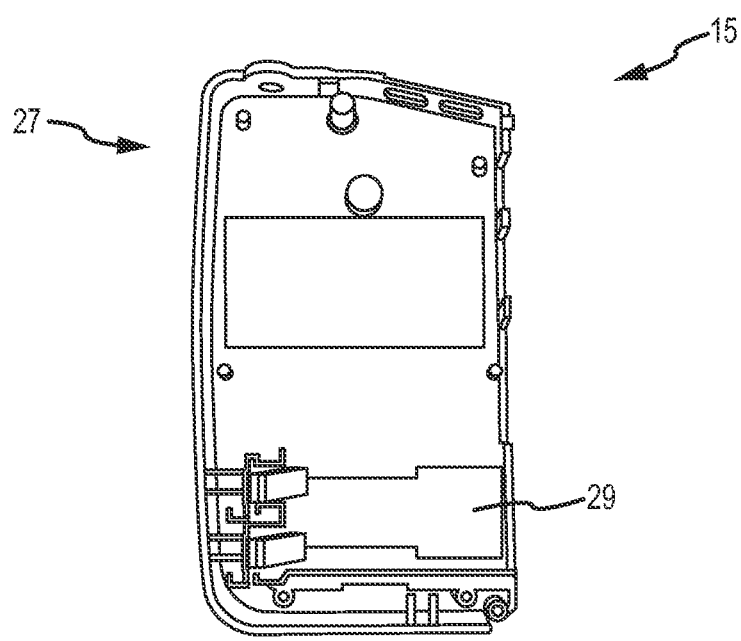
Figure 3G:
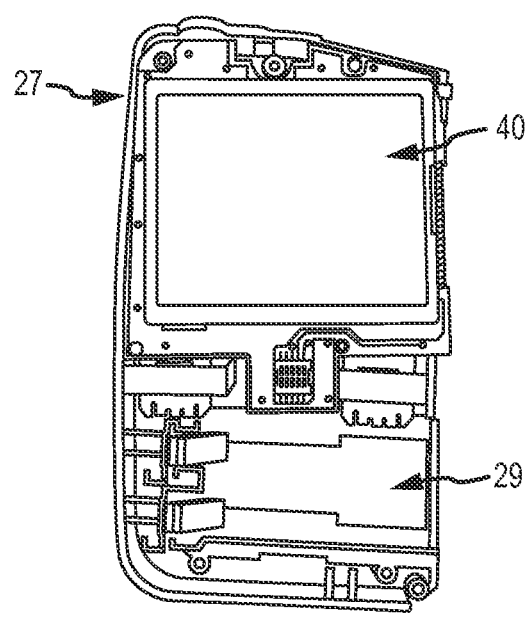
FIG. 3G is a top plan view of the inside back portion of the housing pulse generator of FIG. 3A, wherein some electrical components and a display are shown.
Figure 3I:
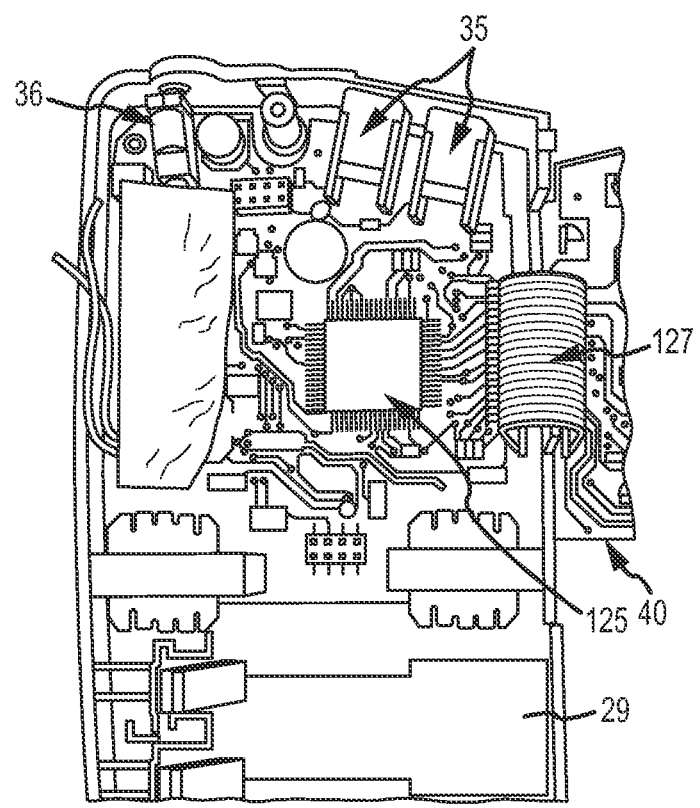
FIGS. 3I-3J depict an expanded view of the electrical components shown in FIG. 3H.
Figure 3J:
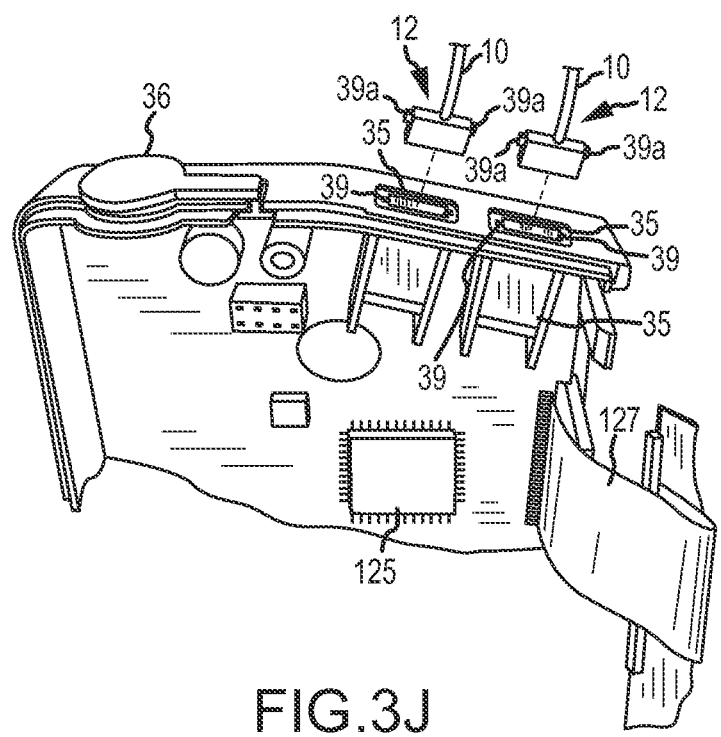
Figure 3K:
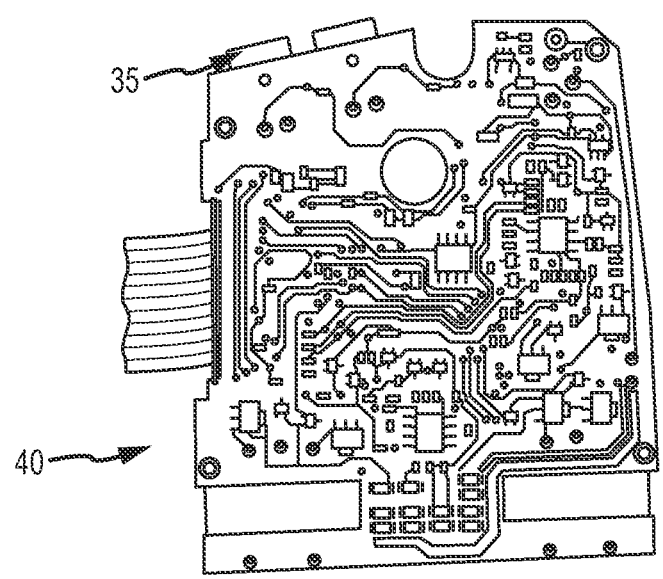
FIG. 3K is a back plan view of the electrical components shown in FIGS. 3I-3J.
Figure 3L:
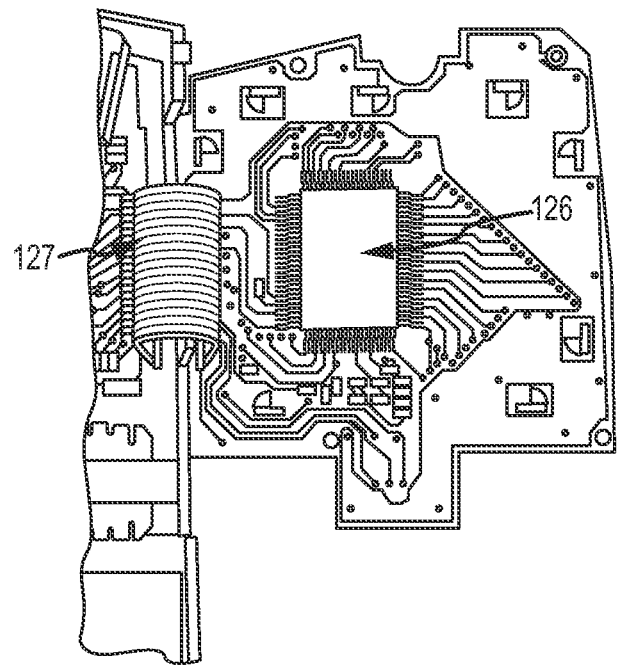
FIG. 3L is a back plan view of the display and associated electrical components of FIG. 3H.

As can be seen in at least FIGS. 3E-1 and 3E-2, the pulse generator 15 may also include a power inlet port 36. The power inlet port 36 is configured to accept a connector from a power supply source, such as a DC power supply. In use, the pulse generator is powered by a battery and/or the power supply source (not shown).

In some embodiments, the pulse generator 15 is powered by a rechargeable lithium-ion 9V battery that is received in a battery cavity 29 of the body 25, as shown in at least FIGS. 3F-2, 3G and 3I. In some embodiments, the generator 15 is powered by lithium-polymer batteries.

As can be understood from FIGS. 3G, 3H, 3I, 3K, 3L and others, the pulse generator 15 also includes a display 40, such as an LED or LCD screen, to display a graphical user interface (GUI). The display may also be controlled by a microcontroller 126 on a display PCB 128. The display PCB 128 is coupled to the pulse generator microcontroller 125 on the microcontroller PCB 129 via a ribbon 127. The display 40 may be manipulated by user control features 30 that allow the physician and patient to select specific graphical menus. The user control features 30 may be generated on the GUI or may be features of or integrated with the case 25. The GUI may include a touch-screen interface, thereby allowing the user-patient to make a selection by touching it on the screen.

The GUI is used to control the electric stimulation parameters and, in some embodiments, may provide password protection. In one embodiment, two levels of password protection are provided. The first level of protection allows patients to change their stimulation parameters within a range that has been predetermined by qualified medical personnel, which may be limited to electrical current amplitude. The second level of password protection allows qualified medical personnel to limit the range of stimulation parameters available to the patient. In addition to these parameters, qualified medical personnel can select timed therapy regimens of 1 to 16 hours, as well as a continuous stimulation mode.

As can be understood from FIG. 4, the pulse generator is coupled to a power source 100. With reference to FIGS. 3A-3L, in one embodiment, the pulse generator 15 is operably coupled to a battery 100. In other embodiments, the power source may be any suitable power source, such as a fuel cell, or etc. In some embodiments, the battery 100 is rechargeable using inductive coupling to the patient's home base station. In some embodiments, the rechargeable battery has a 5 year life. The battery 100 and/or the pulse generator 25 may be operably coupled to a (an additional) power supply or charging station 115, such as the patient's home base station. The battery may be an internal lithium rechargeable battery. In one embodiment, the battery has a capacity up to 1000 mA-hours to last a minimum of 36-48 hours between charges. In some embodiments, the pulse generator may also be used in conjunction with the patient recharging station. In one embodiment, the patient recharging station is a bedside stand and recharging facility for storing the device when not in use. The pulse generator 15 is also operably coupled to electrodes 105 (which may be a part of the electrode assembly 10). In some embodiments, the pulse generator 15 may be coupled to the electrodes 105 via the wire 20 or the generator 15 and the electrodes 105 may be wirelessly coupled. In some embodiments, the electrodes 105 and the generator 15 may be a single unit, e.g. the generator 15 is connected directly to and positioned generally on the electrode. The electrode 105 may be replaced daily (or at another appropriate time) but the generator 15 is reusable. In other embodiments, the generator may be intended for a single-time use (non-reusable). The electrodes 105 may provide data to the pulse generator 15 and the generator 15 may, in turn, produce an output 120, such as notification to the patient that an electrode has become disconnected or that an electrode needs to be repositioned. In some embodiments, the pulse generator 15 may further include a digital display of some or all parameters including output current and skin impedance. As indicated in FIG. 4, the pulse generator 15 is in communication with a storage medium 110. In some embodiments, the storage medium is integrated with the pulse generator. In some embodiments, the storage medium is a separate component of the system. The pulse generator 15 includes a microcontroller 125, or other suitable processor, for receiving and executing instructions from a storage medium 110, such as a non-volatile storage medium, magnetic storage medium, optical storage medium, flash memory, other computer readable medium, or suitable memory device. A processor, such as the microcontroller 125, may control operation of the pulse generator 15. The processor 125 may be any electronic device cable of processing, receiving and/or transmitting instructions. For example, the processor 125 may be a microprocessor, a microcomputer and the like. Various features to be implemented by the programmable microcontroller 125 of the pulse generator 15 are discussed in more detail with reference to FIG. 5.

FIG. 5 is a flow chart illustrating one embodiment of a method 200 for operating a pulse generator in accordance with the present disclosure. The method 200 may be performed by the microcontroller 125, or other suitable processor executing instructions from a computer readable medium. It should be appreciated that the operations of the method 200 may be performed in the order illustrated, in another suitable order and/or one or more operations may be performed simultaneously. Moreover, in some embodiments, the method 200 may include more or fewer operations than those illustrated.

In operation 205, the pulse generator may be turned on or otherwise activated. As part of this operation, the identity of the intended recipient of the treatment may be verified. That is, use of the pulse generator may be restricted to a specific individual patient for which TNS treatment has been prescribed, and may not be used by other unauthorized individuals. In some embodiments, a multi-digit personal code (PIN) that may be chosen by the patient and set by the physician. In some embodiments, the PIN may be a 5 digit code. The patient enters the PIN before treatment will begin. If there are more than a predetermined number of incorrect guesses (e.g. 5) of the PIN, the generator ceases to be operational (e.g. "locks up") for 1 hour (or other appropriate time) and logs the event. In some embodiments, only one treatment session per day is permitted. In other embodiments, a biometric identification system (e.g. a thumbprint) may be used instead of a PIN. The PIN or biometric ID prevent sharing of devices and may reduce the risk of clinically inappropriate use by other individuals.

In operation 210, an electrode check is made. The electrode check may be performed at the start of the session and may monitor the electrode assembly for operational anomalies. In one embodiment, the pulse generator may include a "handshake" with a chip or circuit on or associated with the electrode, which downloads a serial number, and detects the model of electrode (e.g. a single pair of contacts or separate R/L pairs of contacts). In the operation, the pulse generator checks to determine if it is connected to the electrodes, the electrodes are properly positioned and the like. In some embodiments, the pulse generator may further deliver stimulation signals to the electrode contacts within an electrode assembly in this operation and may set the "used" bit on the electrode assembly at the end of treatment to enforce single use. This ensures that the gel on the contacts is uncontaminated, as damaged gel could produce current flow irregularities ("hot spots") leading to skin injury from excessive local current flow. If the electrode check is ok (e.g. the electrodes are connected, properly positioned and the like), then the method may proceed to operation 215-pulse generation.

If the electrode check is not ok, then the method proceeds to operation 212. For example, if impedance suddenly becomes high, then a signal will be sent to indicate that the electrodes have become disconnected ("infinite" impedance). If impedance is low or excessively low, then the user is prompted to relocate the electrodes (e.g. there is a need to reposition the electrode to ensure skin safety). In some embodiments, the signal may also be sent or alternatively sent to a physician or other care provider and/or a designated family member. The pulse generator may signal such trouble conditions. Treatment may be terminated or the patient may adjust the electrodes as indicated and restart treatment (e.g. turning the pulse generator off and then back on or the pulse generator may perform another electrode check).

The method 200 may next proceed to operation 215. A pulse may be generated in this operation. The pulse characteristics may include: (1) controlled-current rectangular pulses, to one or two channels, with one or more of the following characteristics: (a) maximum deliverable current of 30 mA/channel (or as defined elsewhere in this disclosure), (b) physician may set upper and lower bounds for each patient, ranging from 0.3 to 30 mA (e.g. default settings of 1 mA lower bound, 20 mA upper bound), (c) user-adjustment of actual current delivery within that range to allow setting for comfort, (d) provision for a single bipolar channel, with user ability to swap polarity (e.g. shift from "right side=positive/left side=negative" to the opposite) and (e) provision for a pair of bipolar channels with user ability to swap polarity (e.g. right and left channels are separate pairs, each with a lower and upper electrode contact, and options are "upper pos./lower neg." and "lower pos./upper neg." arrangements); (2) pulse width (duration) from 10 to 3000 μs, which may be set by physician (e.g. default 250 μs); (3) repetition rate frequency ranging from 10 to 300 Hz, which may be set by physician; (4) duty cycle adjustable by physician, setting the seconds on and seconds off periods, each variable from 5 s to 60 s in, for example, 5 s steps (e.g. default 30 s on/30 s off); and (5) session length of 1 to 23 hours (e.g. default 8 hours). Various embodiments may permit adjustment or programming of any or all of the foregoing. In some embodiments, the operation includes 2-channels, and operates at the following parameters: frequency 1-300 Hz, pulse duration 50-500 μs, duty cycle 1-100%. The two channels may be configured to provide either synchronous or asynchronous stimulation. In some embodiments, the pulse generated in this operation may be transmitted across two separate channels or multiple unique pulses may be generated and carried across a separate channel. In some embodiments, the pulse wave form may be shaped through programmable settings for pulse duration, frequency, and duty cycle and the like. These programmable settings may be adjusted only by a physician or other authorized caregiver in certain embodiments. Generally, reprogramming of operational parameters discussed herein may be restricted to parties supplying an appropriate password or other credential, such as a biometric indicator. This feature may prevent patients from using the generator at settings contrary to medical prescription or outside of FDA labeling.

As can be understood from the previous section, the programmable microcontroller 125 limits output current. That is, the patient-adjustable current is limited to approximately less than 35 mA to maximize tolerance, minimize current and charge density, and minimize any potential for current penetration through the skull. The controller 125 may deliver true square-wave charge-balanced output. This may be advantageous because existing commercial TENS units have asymmetric output, resulting in irregular stimulation, and risk for formation of hotspots, which may contribute to skin irritation or injury. In some embodiments, asymmetric waveforms may be employed, provided the specific signals are safe.

The microcontroller may be set to a range of outputs. In one embodiment, the range may be set to approximately between 2.5 mA and approximately 7 mA. In one embodiment, the microcontroller limits the output current to approximately 7 mA, and the patient may adjust the current within a range below 7 mA. In another embodiment, the microcontroller can limit the output current to a narrow range (e.g. to ensure safety and compliance) of between approximately 2.5 mA to approximately 5 mA using an external electrode two or four contact electrode. In this way, the patient is prevented from delivering current at too high or too low of an output. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, 7 mA, or 5 mA. Without wishing to be limited by any particular theory, it is believed that higher currents, depending on the size and impedance of the electrode, may cause pain, discomfort and/or skin irritation for the patient.

The method 200 may further include an operation 220 in which the activity of the pulse generator is logged. The logging of use operation 220 may include: (1) recording data for each session, such as: (a) session start date-and-time; (b) session stop date-and-time (actual time treatment was ended), (c) user-adjustable setting (e.g. actual current delivered), and (d) session-specific data (e.g. max & min impedance, electrode & configuration). The operation 220 may also include: logging operational anomalies (e.g. electrode disconnects, low impedances, lock-outs for attempts at unauthorized use, etc.), transferring data to the physician's programming console and may include the capacity to store 6 months of treatment data. In other embodiments, less than 6 months or greater than 6 months of data may be stored. A patient's compliance (adherence) and usage is monitored via, e.g., logfiles. Such monitoring may be used to help monitor use patterns in assessing a patient's response to treatment (e.g., a poor clinical response may be linked to using the device less often than prescribed).

In some embodiments, the pulse generator may also signal operational parameters to the patient. This may be part of the logging of use operation 220 or may be part of a different or a separate operation. For example, a signal may be sent if the user is locked out for PIN guessing, a signal may indicate the minutes until the generator is unlocked. In another example, a signal may be sent if the need for physician follow-up reprogramming is coming up and the signal indicates how many more days of treatment remain before a "refill" date is reached. The pulse generator may also display current time and date in the time zone where programmed, display time left in current session (hr:min) and/or display time needed in charger (hr:min) to be ready for the next session.

The method 200 may further include an operation 225 in which the end of the authorized treatment period is signaled. In one embodiment, several weeks (e.g. default is 3 weeks) prior to the end of the treatment period (e.g. default is 3 months), the operation 230 notifies the user that the treatment period is nearing its end and that a follow up visit with the prescribing doctor for clinical assessment and reprogramming needs to be scheduled. In one embodiment, notification is made at the start of the session. In subsequent weeks, the patient is notified that one less week remains to schedule the visit. In the final week, a daily count-down of days remaining is provided. At the final treatment in the authorized period, the user is notified that this is the last treatment.

In operation 230, treatment is terminated. Use of the generator may be suspended (e.g. user is locked out) until reprogrammed by a physician or physician programming console or use of the generator may be terminated.

In use, in one embodiment, the electrode assembly 10 is positioned over the forehead of the patient 5. In some embodiments, the electrode assembly 10 may include an insulative connection region which helps to line up the assembly 10 with the midline of the nose of the patient 5. In some embodiments, the electrode assembly 10 is placed over the supraorbital foramina, located over the orbital ridge approximately 2.1-2.6 cm lateral to nasal midline. In one embodiment, the electrode assembly 10 is then connected to a pulse generator 15 via the electrical cable 20. In other embodiments, the electrode assembly is connected to the pulse generator 15 via a wireless connection. In some embodiments, the electrode assembly may be a subcutaneous or percutaneous implantable electrode assembly. In the "percutaneous" form, the electrodes are inserted through the skin but the generator remains external; there may be a lead wire which exits through the skin, or the electrode may be entirely within the skin tissue and they are coupled to a non-implanted generator through, e.g., inductive coupling. The pulse generator then provides stimulation according to methods as described herein.

As indicated above, the pulse generator disclosed herein may be used to treat a disorder or condition in a patient using trigeminal nerve stimulation (TNS). Broadly speaking, the method of treatment includes positioning external electrodes over or near at least one of the foramina or branches of the trigeminal nerve (FIG. 1A-1B), and stimulating the electrodes using a stimulator or pulse generator as disclosed herein for a fixed time at specified operational parameters. In one embodiment, the external electrodes are positioned over the foramina of the supraorbital or ophthalmic nerves (FIG. 1A, Foramen 1). In alternative embodiments, the electrode assembly 10 can be positioned over the foramina of the maxillary nerves (FIG. 1A, Foramen 2) or the mandibular nerves (FIG. 1B, Foramen 3). In yet other embodiments, the stimulation can be unilaterally applied to one foramen of the trigeminal nerves. In other embodiments, electrodes may be positioned at a region of the patient's face (on the right and/or left side) corresponding with the supratrochlear nerve, infratrochlear nerve, zygomaticotemporal, zygomaticofacial, zygomaticoorbital, mentalis, nasal and/or auriculotemporal nerves and/or their respective foramina. In other embodiments, subcutaneous implantable electrodes may be used with the pulse generator as disclosed herein. The programmable microcontroller may be programmed to operate at one or more of the following parameters.

In various embodiments, the stimulation is delivered at a specific pulse width or range of pulse widths (or pulse duration). The stimulation can be set to deliver pulse widths in the range greater than and/or less than one or more of 50 µs, 60 µs, 70 µs, 80 µs, 90 µs, 100 µs, 125 µs, 150 µs, 175 µs, 200 µs, 225 µs, 250 µs, up to 500 µs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 µA and an upper limit of about 30 mA-35 mA, depending on the surface area of the electrodes, inter-electrode distance, the branch(es) stimulated, and the modeling data as described above. In various embodiments, the amplitude can be in a range greater than and/or less than one or more of 50 µA, 75 µA, 100 µA, 125 µA, 150 µA, 175 µA, 200 µA, 225 µA, 250 µA, 275 µA, 300 µA, 325 µA, 350 µA, 375 µA, 400 µA, 425 µA, 450 µA, 475 µA, 500 µA, 525 µA, 550 µA, 575 µA, 600 µA, 625 µA, 650 µA, 675 µA, 700 µA, 725 µA, 850 µA, 875 µA, 900 µA, 925 µA, 950 µA, 975 µA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA and 20 mA. In some embodiments, the current amplitudes are less than 7 mA, or less than 6 mA, depending on the size, impedance, resistance, or configuration of the electrode(s). In some embodiments, the current amplitude is between about 2.5 mA and about 5 mA. Those of skill in the art will recognize that one or more of the above amplitudes can be used as a border of a range of amplitudes.

In various embodiments, the stimulation can be delivered at one or more frequencies, or within a range of frequencies. The stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 120 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles. The stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification and examples provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A system for trigeminal nerve stimulation comprising:
   a storage medium;
   a pulse generator comprising:
      a user control configured to receive a user adjustment; and
      a microcontroller coupled to the storage medium and executing instructions from the storage medium, the microcontroller configured to:
         receive electric stimulation parameters comprising at least one user-set parameter and at least one physician-set parameter, the at least one user-set parameter comprising a current amplitude responsive to the user adjustment of the user control, and the at least one physician-set parameter comprising an upper bound and a lower bound for the current amplitude;

operate the pulse generator to produce electrical pulses according to the electric stimulation parameters during treatment sessions; and record a log of use for monitoring a patient's adherence to a treatment plan;

a power source; and an electrode assembly communicatively coupled to the pulse generator.

2. The system of claim 1, further comprising a power supply or charging station.

3. The system of claim 1, wherein the power source is a battery electrically coupled to the pulse generator.

4. The system of claim 1, wherein said electrode assembly is wirelessly coupled to the pulse generator.

5. The system of claim 1 wherein said electrode assembly is coupled to the pulse generator via a connector or lead wire.

6. The system of claim 1, wherein the electrode assembly is a two-contact electrode.

7. The system of claim 1, wherein the electrode assembly is a four-contact electrode.

8. The system of claim 1, wherein the log includes a duration of the treatment sessions, a start time for each of the treatment sessions, an end time for each of the treatment sessions, a setting for the at least one user-set parameter for each of the treatment sessions, and an impedance for each of the treatment sessions.

9. A method for operating a pulse generator having a processing device for stimulating at least one trigeminal nerve branch using the pulse generator, the method comprising:

receiving, by the processing device, electric stimulation parameters comprising at least one user-set parameter and at least one physician-set parameter, the at least one user-set parameter comprising a current amplitude responsive to a user adjusting a user control, and the at least one physician-set parameter comprising an upper bound and a lower bound for the current amplitude;

producing, by the pulse generator, electrical pulses according to electric stimulation parameters during treatment sessions; and recording, by the processing device, a log of use of for monitoring a patient's adherence to a treatment plan.

10. The method of claim 9, wherein the electric stimulation parameters comprise a frequency of 1-300 Hz, pulse duration of 50-500 microseconds, and a duty cycle of 1-100%.

11. The method of claim 9, wherein the log includes a duration of the treatment sessions, a start time for each of the treatment sessions, an end time for each of the treatment sessions, a setting for the at least one user-set parameter for each of the treatment sessions, and an impedance for each of the treatment sessions.

12. The system of claim 1, wherein the microcontroller is configured to detect a model of the electrode assembly.

13. The system of claim 12, wherein the microcontroller is configured to detect the model of the electrode assembly by downloading a serial number of the electrode assembly.

14. The system of claim 1, wherein the pulse generator is configured to set a used bit on the electrode assembly at the end of each of the treatment sessions.

15. The method of claim 9, further comprising detecting a model of an electrode assembly.

16. The method of claim 15, wherein the detecting comprises downloading a serial number of the electrode assembly.

17. The method of claim 9, further comprising setting a used bit on an electrode assembly at the end of each of the treatment sessions.

* * * * *